(12) United States Patent
Brujic et al.

(10) Patent No.: US 9,981,237 B2
(45) Date of Patent: May 29, 2018

(54) HIGHER ORDER MULTIPLE EMULSIONS

(71) Applicant: New York University, New York, NY (US)

(72) Inventors: Jasna Brujic, New York, NY (US); Martin Haase, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days. days.

(21) Appl. No.: 14/829,578

(22) Filed: Aug. 18, 2015

(65) Prior Publication Data

US 2016/0051954 A1 Feb. 25, 2016

Related U.S. Application Data

(60) Provisional application No. 62/039,166, filed on Aug. 19, 2014.

(51) Int. Cl.
*B01J 13/00* (2006.01)
*B01J 13/06* (2006.01)
(Continued)

(52) U.S. Cl.
CPC ............. *B01J 13/00* (2013.01); *A61K 8/11* (2013.01); *A61K 8/14* (2013.01); *A61K 9/113* (2013.01);
(Continued)

(58) Field of Classification Search
CPC ....... A61K 9/113; B01F 3/0807; B01F 5/045; B01F 13/0059; B01J 13/06; B01J 13/02
See application file for complete search history.

(56) References Cited

U.S. PATENT DOCUMENTS 5,976,405 A * 11/1999 Clikeman ............ C09K 19/544
252/299.01
6,683,041 B1 * 1/2004 Nissing ................ C11D 17/048
510/108
(Continued)

FOREIGN PATENT DOCUMENTS

AU WO 2010121307 A1 * 10/2010 ............ B01F 3/0807

OTHER PUBLICATIONS

Haase et al. Angew. Chem. Int. Ed. 2014, 53, 11793-11797.*
(Continued)

*Primary Examiner* — Michael A Salvitti
(74) *Attorney, Agent, or Firm* — Foley & Lardner LLP

(57) ABSTRACT

Multiple emulsions with an "onion" topology are useful vehicles for drug delivery, biochemical assays, and templating materials. They can be assembled by ternary liquid phase separation using microfluidics, but the control over their design is limited because the mechanism of their creation is unknown. Here it is shown that phase separation occurs via self-similar cycles of mass transfer, spinodal decomposition or nucleation, and coalescence into multiple layers. Mapping out the phase diagram demonstrates a linear relation between concentric layer diameters, whose slope depends on the initial ternary composition and the molecular weight of the surfactant. These general rules quantitatively predict the number of droplet layers (multiplicity). Further, self-assembly routes for polymer capsules and liposomes are provided with techniques to assemble lipid-stabilized droplets with ordered internal structures.

11 Claims, 13 Drawing Sheets

(51) Int. Cl.
| | |
|---|---|
| B01J 13/02 | (2006.01) |
| A61K 9/113 | (2006.01) |
| B01J 13/12 | (2006.01) |
| B01F 5/04 | (2006.01) |
| B01F 13/00 | (2006.01) |
| B01F 3/08 | (2006.01) |
| A61Q 19/00 | (2006.01) |
| A61K 8/11 | (2006.01) |
| A61K 8/14 | (2006.01) |

(52) U.S. Cl.
CPC ............ *A61Q 19/00* (2013.01); *B01F 3/0807* (2013.01); *B01F 5/045* (2013.01); *B01F 13/0059* (2013.01); *B01J 13/02* (2013.01); *B01J 13/06* (2013.01); *B01J 13/125* (2013.01); *A61K 2800/10* (2013.01); *A61K 2800/80* (2013.01)

(56) References Cited

U.S. PATENT DOCUMENTS

| | | | |
|---|---|---|---|
| 2009/0012187 A1* | 1/2009 | Chu | A61K 9/113 516/54 |
| 2009/0131543 A1* | 5/2009 | Weitz | A61K 9/113 516/54 |
| 2011/0305761 A1* | 12/2011 | Shum | A61K 9/1273 424/489 |
| 2013/0168885 A1* | 7/2013 | Omiatek | A61K 9/1277 264/4.1 |
| 2016/0000886 A1* | 1/2016 | Parker | A61K 9/1273 424/491 |
| 2016/0051954 A1* | 2/2016 | Brujic | B01J 13/00 516/54 |
| 2016/0263034 A1* | 9/2016 | Khan | A61K 9/145 |
| 2016/0332131 A1* | 11/2016 | Lee | B01J 13/10 |

OTHER PUBLICATIONS

Choi et al. Adv. Mater. 2013, 25, 2536-2541.*
Alred, P.A., et al., "Application of temperature-induced phase partitioning at ambient temperature for enzyme purification", J. Chromatogr. A, 1994, 659:289-298.
Anna, S.L., et al., "Formation of dispersions using flow focusing in microchannels", Appl. Phys. Lett., Jan. 20, 2003, 82(3):364-366.
Bencherif, S.A., et al., "Injectable preformed scaffolds with shape-memory properties", Proc. Natl. Acad. Sci., 2012, 109(48):19590-19595.
Booth, D.R., et al., "Instability, unfolding and aggregation of human lysozyme variants underlying amyloid fibrillogenesis", Nature, Feb. 27, 1997, 385:787-793.
Cheeseman, I.M., et al., "A Combined Approach for the Localization and Tandem Affinity Purification of Protein Complexes from Metazoans", Sci. STKE, Jan. 11, 2005, 266(pl1):1-15.
Chiti, F., et al., "Protein Misfolding, Functional Amyloid, and Human Disease", Ann. Rev. Biochem., 2006, 75:333-366.
Choi, C-H., et al., "Microfluidic Design of Complex Emulsions", Chem. Phys. Chem., 2014, 15:21-19.
Cleland, J.L., et al., "Polyethylene Glycol Enhanced Protein Refolding", Nat. Biotechnol., Sep. 1992, 10:1013-1019.
Da Silva, L.H.M., et al., "Calorimetric Investigation of the Formation of Aqueous Two-Phase Systems in Ternary Mixtures of Water, Poly(ethylene oxide) and Electrolytes (or Dextran)", J. Phys. Chem. B, 2000, 104:10069-10073.
Dhulesia, A., et al., "Local Cooperativity in an Amyloidogenic State of Human Lysozyme Observed at Atomic Resolution", J. Am. Chem. Soc., 2010, 132:15580-15588.
Dobson, C.M., "Protein folding and misfolding", Nature, Dec. 18-25, 2003, 426:884-890.

Fele, L., et al., "Partition Coefficients of Proteins in Poly(ethylene glycol) + Dextran + Water at 298 K", J. Chem. Eng. Data, 1996, 41:331-334.
Gebbink, M.F.B.G., et al., "Amyloids—A Functional Coat for Microorganisms", Nat. Rev. Microbiol., Apr. 2005, 3:333-341.
Goldstein, R.E., "On the theory of lower critical solution points in hydrogen-bonded mixtures", J. Chem. Phys., May 15, 1984, 80(10):5340-5341.
Hanazawa, T., et al., "Effect of Oil Droplets and Their Solid/Liquid Composition on the Phase Separation of Protein—Polysaccharide Mixtures", Langmuir, 2013, 29:9841-9848.
Holtze, C., et al., "Biocompatible surfactants for water-in-fluorocarbon emulsions", Lab on Chip, 2008, 8:1632-1639.
Hsu, C.C., et al., "Thermodynamics of Polymer Compatibility in Ternary Systems", Macromolecules, May-Jun. 1974, 7(3):320-324.
Hsu, J. C-C., et al., "Thioflavin T and Its Photoirradiative Derivatives: Exploring Their Spectroscopic Properties in the Absence and Presence of Amyloid Fibrils", J. Phys. Chem. B, 2013, 117:3459-3468.
Knowles, T.P.J., et al., "Nanomechanics of functional and pathological amyloid materials", Nature Nanotechnology, Aug. 2011, 6:469-479.
Knowles, T.P.J., et al., "The amyloid state and its association with protein misfolding diseases", Nat. Rev. Mol. Cell Biol., Jun. 2014, 15:384-396.
Kroner, K.H., et al., "Technical Aspects of Separation Using Aqueous Two-Phase Systems in Enzyme Isolation Processes", Biotechnol. Bioeng., 1978, 20:1967-1988.
Langer, R., et al., "Designing materials for biology and medicine", Nature, Apr. 1, 2004, 428:487-492.
Liu, C.L., et al., "Separation of proteins and viruses using two-phase aqueous micellar systems", J. Chromatogr. B: Biomed. Sci. Appl., 1998, 711:127-138.
Liu, Y., et al., "Concentration Dependence of the Interfacial Tension for Aqueous Two-Phase Polymer Solutions of Dextran and Polyethylene Glycol", Langmuir, 2012, 28:3831-3839.
Ma, S., et al., "Fabrication of Microgel Particles with Complex Shape via Selective Polymerization of Aqueous Two-Phase Systems", Small, 2012, 8(15):2356-2360.
Madeira, P.P., et al., "Salt effects on solvent features of coexisting phases in aqueous polymer/polymer two-phase systems", J. Chromatogr. A, 2012, 1229:38-47.
Mattsson, J., et al., "Soft Colloids make strong glasses", Nature, Nov. 5, 2009, 462:83-86.
Menegatti, S., et al., "Alkaline-stable peptide ligand affinity adsorbents for the purification of biomolecules", J. Chromatogr. A, 2012, 1245:55-64.
Minton, A.P., "Quantitative Assessment of the Relative Contributions of Steric Repulsion and Chemical Interactions to Macromolecular Crowding", Biopolymers. 2013, 99(4):239-244.
Munishkina, L.A., et al., "The effect of macromolecular crowding on protein aggregation and amyloid fibril formation", J. Mol. Recognition, 2004, 17:456-464.
Murray, B.S., et al., "The effect of nanoparticles on the phase separation of waxy corn starch + locust bean gum or guar gum", Food Hydrocolloids, 2014, 42:92-99.
Otsuka, H., et al., "PEGylated nanoparticles for biological and pharmaceutical applications", Adv. Drug Deliv. Rev, 2003, 55:403-419.
Peters, T.J., "Book reviews: Partition of Cell Particles and Macromolecules", Cell Biochem. Funct., 1987, 5:233-234.
Rosa, P., et al., "Aqueous two-phase systems: A viable platform in the manufacturing of biopharmaceuticals", J. Chromatogr. A, 2010, 1217:2296-2305.
Schwarz-Linek, J., et al., "Phase separation and rotor self-assembly in active particle suspensions", Proc. Natl. Acad. Sci., Mar. 13, 2012, 109(11):4052-4057.
Song, Y., et al., "All-aqueous multiphase microfluidics", Biomicrofluidics, 2013, 7:061301 1-12.
Song, Y., et al., "Monodisperse w/w/w Double Emulsion Induced by Phase Separation", Langmuir, 2012, 28:12054-12059.

(56) References Cited

OTHER PUBLICATIONS

Torok, B., et al., "Diaryl Hydrazones as Multifunctional Inhibitors of Amyloid Self-Assembly", Biochemistry, Feb. 19, 2013, 52(7):1137-1148.
Vendruscolo, M., et al., "Protein Solubility and Protein Homeostasis: A Generic View of Protein Misfolding Disorders", Cold Spring Harbor Perspect. Biol., 2011, 3:a010454 1-12.
Zheng, B., et al., "Formation of Droplets of Alternating Composition in Microfluidic Channels and Applications to Indexing of Concentrations in Droplet-Based Assays", Anal. Chem., 2004, 76:4977-4982.
Haase, M.F., et al., "Tailoring of High-Order Multiple Emulsions by the Liquid-Liquid Phase Separation of Ternary Mixtures", Angew. Chem., 2014, 126:11987-11991.
Shimanovich, U., et al., "Multiphase Protein Microgels", Macromol. Biosci., 2015, 15(4):501-508.
Abate, A., et al., "Patterning microfluidic device wettability using flow confinement", Lab Chip, 2010, 10(14):1774-1776.
Abate, A.R., et al., "High-Order Multiple Emulsions Formed in Poly(dimethylsiloxane) Microfluidics", Small, Sep. 18, 2009, 5(18):2030-2032.
Abbaspourrad, A., et al., "Polymer Microcapsules with Programmable Active Release", J. Am. Chem. Soc., 2013, 135(20):7744-7750.
Chu, L-Y, et al., "Controllable Monodisperse Multiple Emulsions", Angew. Chem. Int. Ed. 2007, 46:8970-8974.
Deng, N-N, et al., "Wetting-induced formation of controllable monodisperse multiple emulsions in microfluidics", Lab Chip, 2013, 13(20):4047-4052.
Feng, L., et al., "Specificity, flexibility and valence of DNA bonds guide emulsion architecture", Soft Matter, 2013, 9(41):9816-9823.
Hadorn, M., et al., "Specific and reversible DNA-directed self-assembly of oil-in-water emulsion droplets", PNAS, Dec. 11, 2012, 109(50):20320-20325.
Hanson, J.A., et al., "Nanoscale double emulsions stabilized by single-component block copolypeptides", Nature, Sep. 4, 2008, 455:85-88.
Kim, S-H, et al., "Double-emulsion drops with ultra-thin shells for capsule templates", Lab Chip, 2011, 11:3162-3166.
Mitragotri, S., et al., "Physical approaches to biomaterial design", J. Natur. Mater., 2009, 8(1):15-23.
Sacanna, S., et al., "Shaping colloids for self-assembly", Nat. Commun., 2013, vol. 4, 6 pages.
Adams, L.L.A., et al., "Single step emulsification for the generation of multi-component double emulsions", Soft Matter, 2012, 8:10719-10724.

Atkin, R., et al., "Preparation of Aqueous Core/Polymer Shell Microcapsules by Internal Phase Separation", Macromolecules, 2004, 37:7979-7985.
Bendova, M., et al., "Liquid Liquid Equilibrium in the Ternary Systems Water Ethanol Dialkyl Phthalate (Dimethyl, Diethyl, and Dibutyl Phthalate) at 298.15 K", J. Chem. Eng. Data, 2001, 46:1605-1609.
Choi, C-H., et al., "One Step Formation of Controllable Complex Emulsions: From Functional Particles to Simultaneous Encapsulation of Hydrophilic and Hydrophobic Agents into Desired Position", Adv. Mater., 2013, 25:2536-2541.
Datta, S.S., et al., "Delayed Buckling and Guided Folding of Inhomogeneous Capsules", Phys. Rev. Lett., Sep. 28, 2012, 109:134302 1-5.
Jeong, W-C., et al., "Microfluidic synthesis of atto-liter scale double emulsions toward ultrafine hollow silica spheres with hierarchical pore networks", Lab Chip, 2012, 12:5262-5271.
Joscelyne, S.M., et al., "Membrane emulsification—a literature review", J. Membrane Sci., 2000, 169:107-117.
Kim, S-H., et al., "One-step Emulsification of Multiple Concentric Shells with Capillary Microfluidic Devices", Angew. Chem. Int. Ed., Sep. 5, 2011, 50(37):8731-8734.
Lee, S.S., et al., "Nonspherical Double Emulsions with Multiple Distinct Cores Enveloped by Ultrathin Shells", ACS Appl. Mater. Interfaces, 2014, 6:1294-1300.
Manoharan, V.N., et al., "Dense Packing and Symmetry in Small Clusters of Microspheres", Science, Jul. 25, 2003, 301(5632):483-487.
Miesch, C., et al., "Nanoparticle-Stabilized Double Emulsions and Compressed Droplets", Angew. Chem. Int. Ed., 2012, 51:145-149.
Shum, H.C., et al., "Double Emulsion Templated Monodisperse Phospholipid Vesicles", Langmuir, 2008, 24:7651-7653.
Shum, H.C., et al., "Multicompartment Polymersomes from Double Emulsions", Angew. Chem. Int. Ed., 2011, 50:1648-1651.
Tu, F., et al., "Controlling the Stability and Size of Double-Emulsion-Templated Poly(lactic-co-glycolic) Acid Microcapsules", Langmuir, 2012, 28:9944-9952.
Yang, S-M., et al., "Synthesis and assembly of structured colloidal particles", J. Mater. Chem., 2008, 18(19):2161-2284.
Yi, G.R., et al., "Recent progress on patchy colloids and their self-assembly", J. Phys.: Condens. Matter, 2013, 25:193101 1-12.
Zhao C-X., et al., "Microfluidic Mass-Transfer Control for the Simple Formation of Complex Multiple Emulsions", Angew. Chem. Int. Ed., 2009, 48(39):7208-7211.
Zhao, C-X., "Multiphase flow microfluidics for the production of single or multiple emulsions for drug delivery", Advanced Drug Delivery Reviews, 2013, 65:1420-1446.
Zydowicz, N., et al., "PMMA microcapsules containing water-soluble dyes obtained by double emulsion/solvent evaporation technique", Polym. Bull., Jan. 2002, 47(5):457-463.

\* cited by examiner

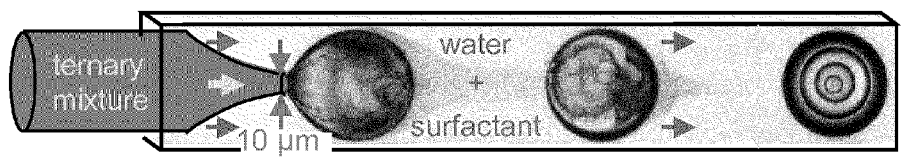
Figures 1A
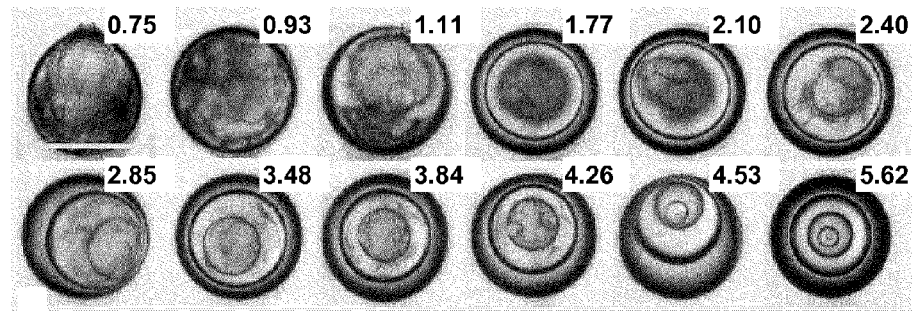
Figures 1B
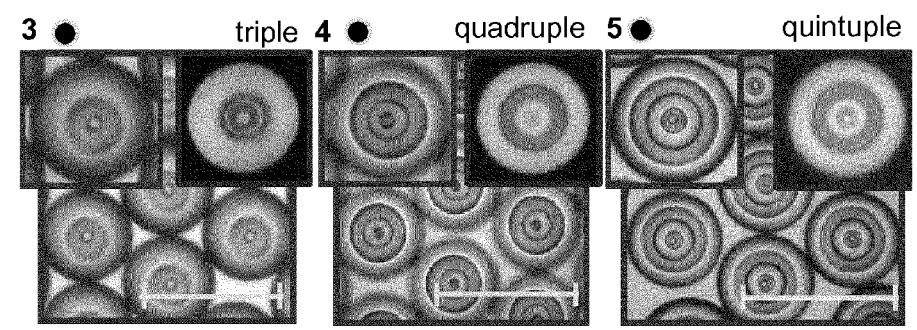
Figures 1C
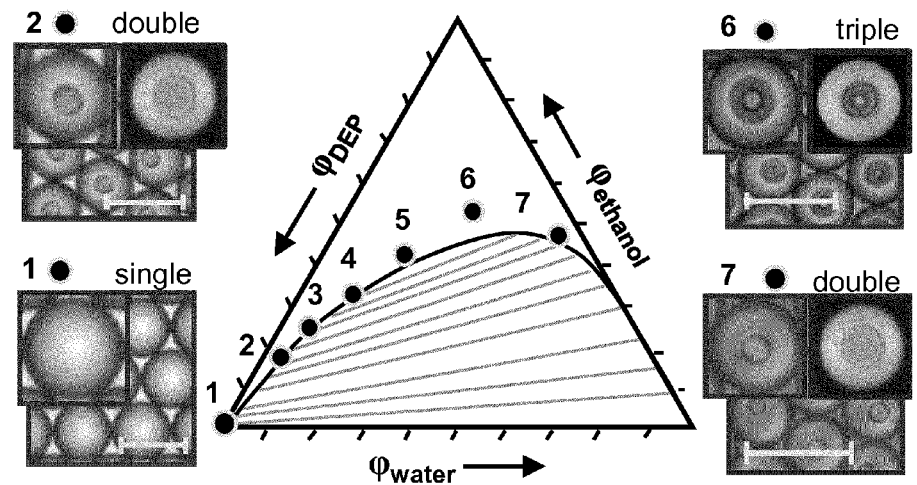

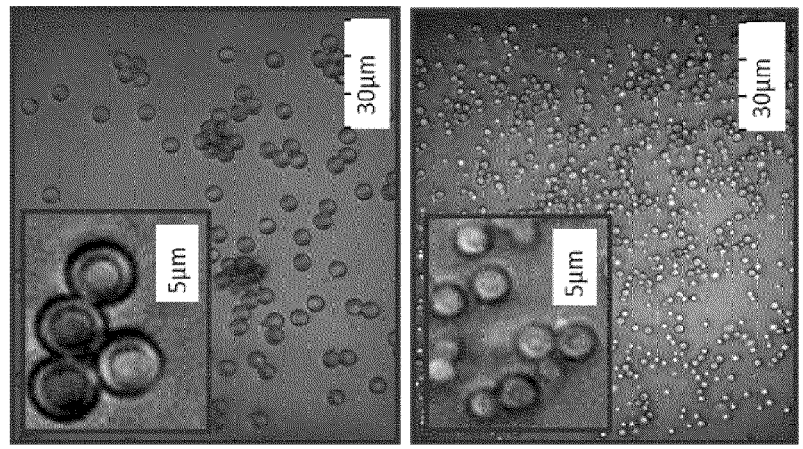
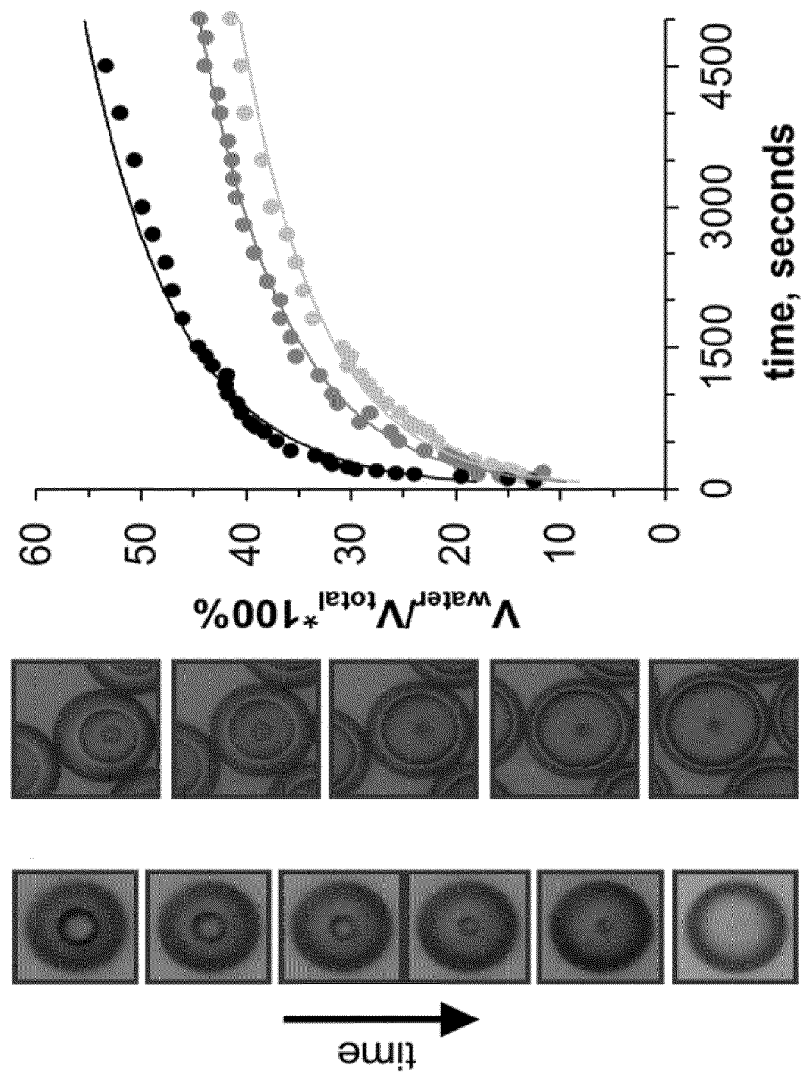
Figure 9C
Figure 9B
Figure 9A

Figure 11A
Figure 11B
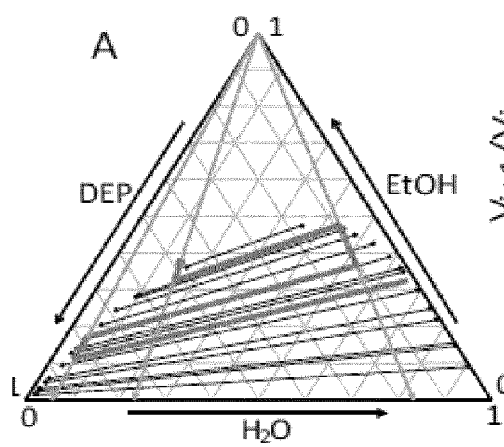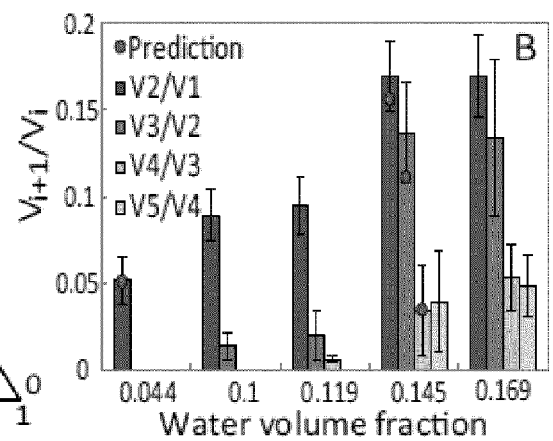
Figure 11C
Figure 11D
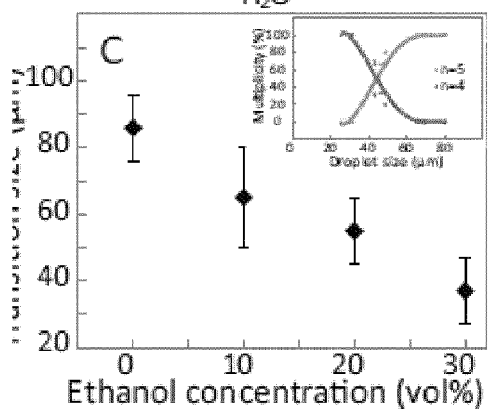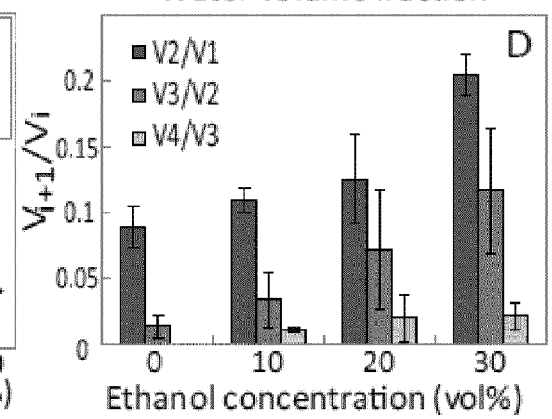

Figure 12A
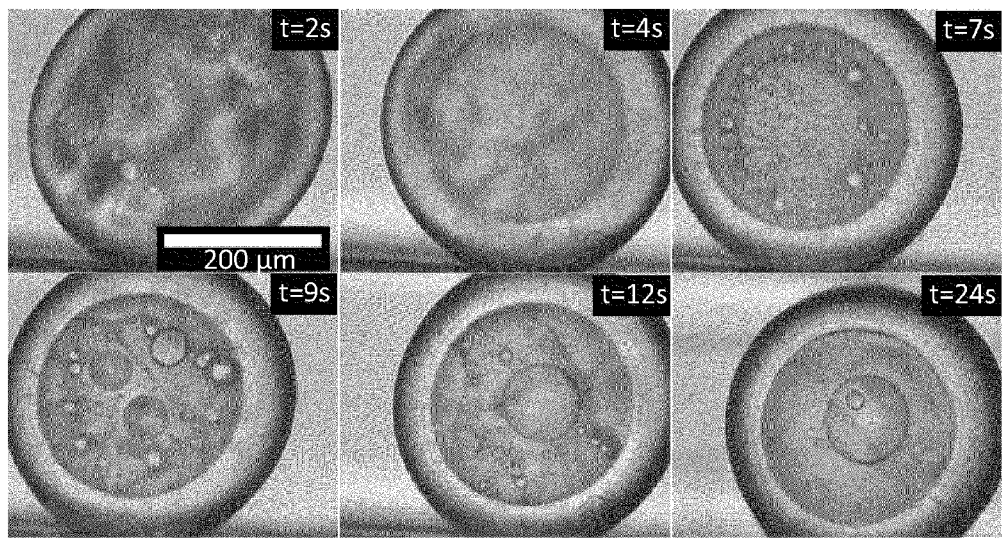
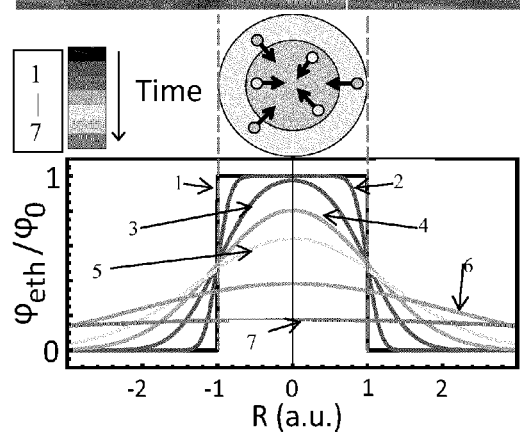
Figure 12B
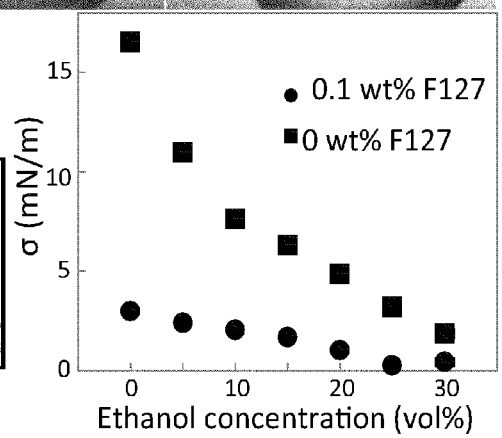
Figure 12C

Figure 13A
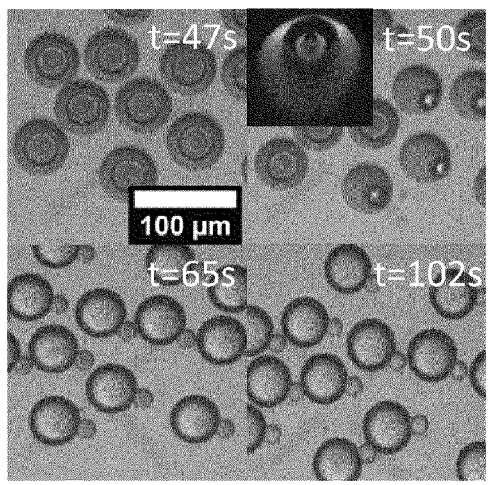
Figure 13B
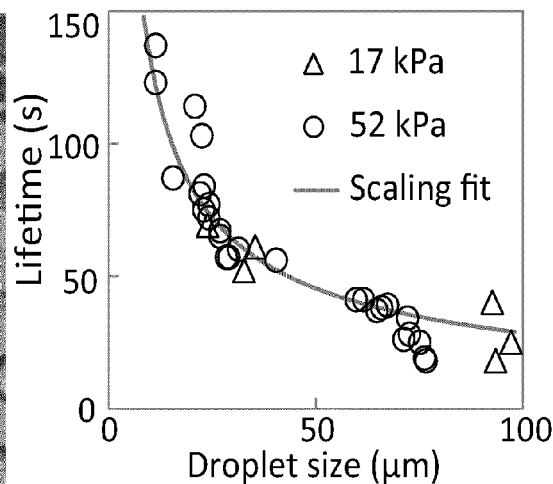
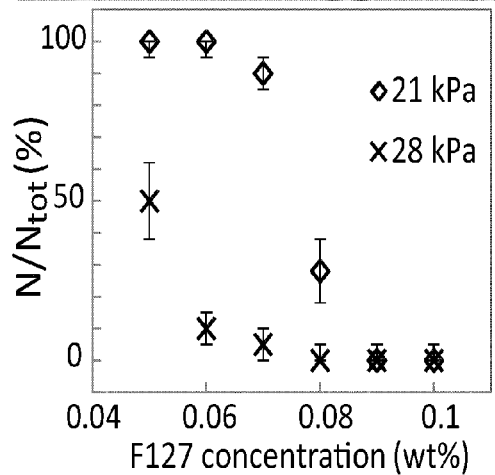
Figure 13C
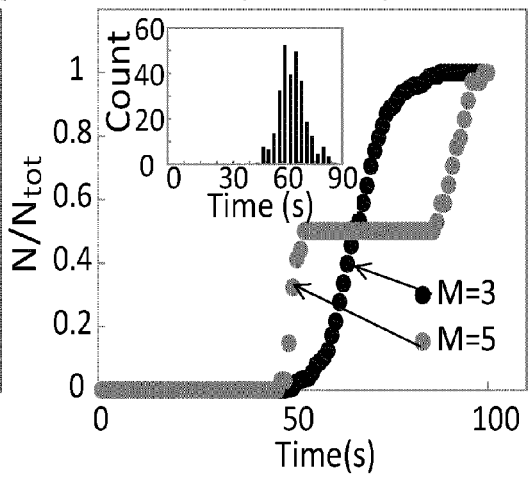
Figure 13D

HIGHER ORDER MULTIPLE EMULSIONS

CROSS-REFERENCE TO RELATED PATENT APPLICATIONS

This application claims priority from Provisional Application U.S. Application 62/039,166, filed Aug. 19, 2014, incorporated herein by reference in its entirety.

STATEMENT OF GOVERNMENT INTEREST

The United States Government has rights in the invention described herein pursuant to National Science Foundation MRSEC program under Grant no. DMR-0820341 for material support and the Career Grant no. 0955621.

FIELD OF THE INVENTION

The present invention generally relates Higher Order Multiple Emulsions. Specifically, embodiments of the present invention relate to phase separation based multiple layered emulsions.

BACKGROUND OF THE INVENTION

Multiple emulsions consist of droplets that encapsulate layers of oil and water from the continuous phase. An active ingredient can be sequestered inside the inner droplets and subsequently released. The layering inside the droplets allows for the release of active ingredients in consecutive steps over long periods of time. Control over the internal structure makes multiple emulsions much sought after in the pharmaceutical, cosmetic and food industries. These emulsions offer versatile templates for structured and patchy colloids, particles of programmable shape, self-assembly tools and biomaterials. Using PDMS microfluidics with multiple channels or glass capillaries with combined flows allows one to mechanically construct high order multiple emulsions. In addition, the use of single surfactants that can stabilise both oil-in-water and water-in-oil layers simplifies their synthesis. These techniques are unsuitable for large-scale production because the number and size of the inner layers are determined by microfluidic flows.

SUMMARY OF THE INVENTION

One implementation of the invention relates to a method of creating an emulsion. A single phase mixture of oil, a polar solvent, and water are dripped through a microcapillary into a continuous phase containing water stream and a surfactant. Phase separating the single phase mixture to form an emulsion having an order greater than 1.

Another implementation relates to a composition of matter. Droplets of a hydrophobic liquid, a polar solvent, and water are dispersed in a continuous phase comprising water and a surfactant.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIGS. 1A-C illustrate: FIG. 1A Schematic of microfluidic glass capillary; FIG. 1B Time series in seconds of a quintuple droplet (DEP/ethanol/water mixture at 0.41/0.42/0.17 vol. %); FIG. 1C Ternary phase diagram shows the effect of composition on the multiplicity of the droplets, depicted in the panels. FITC and nile red dyes label water (blue) and oil (green) layers, respectively. Scale bars are 100 µm.

FIG. 3A Linear dependence of inner layer diameters $d_j$ on the outer diameter $d_1.1$; FIG. 3B Plotting $d_{j+1}$ s a function of the previous layer diameter $d_j$ reveals a linear relation with slope a, where the intercept b gives the smallest double emulsion at b/a. Multiplicity is the number of steps between the line with slope 1 and the mastercurve (blue arrow line); dashed line connects the values of $D_n$; FIG. 3C Slope a increases with the initial water content on the binodal line, as shown by the fit in the inset; FIG. 3D Isomultiplicity lines are in good agreement with the data.

FIG. 4A Double w/o/w emulsions, dyed with FITC (green) and nile red (blue), become water-filled PMMA capsules that buckle upon drying; FIG. 4B Assembly of fluorescently dyed lipids into unilamellar vesicles as the oil evaporates (top, middle panel); vesicles loaded with 1 µm colloids (bottom panel); FIG. 4C Coalescence of triple emulsions; FIG. 4D Multiple emulsions with 2, 4 and 6 water droplets undergo shape changes (top panels) to give ordered inner structures (bottom panel) (The snapshots of shape changes do not correspond to the same droplets).

FIGS. 9A-C depict the size of the inner water droplets can be manipulated post-emulsification; FIG. 9A shows adding salt to the continuous phase (200 mM NaCl) dissolves the inner water droplet. FIG. 9B shows that, conversely, adding salt to the water fraction in the ternary mixture swells the inner water droplet. FIG. 9C shows osmotic swelling stabilizes colloidal size double emulsion droplets (down to one micron).

FIG. 10A shows the microfluidic device having two water drainage structures; FIG. 10B shows the multilayered emulsions forming during the process; FIG. 10C shows the concentrated droplets in a brightfield while FIG. 10D is a fluorescent confocal image of the droplets.

FIG. 11A shows a Quantitative path through the ternary phase diagram calculated from experimental data on droplet shrinkage (the black dots connected by tie lines are experimentally obtained by Haasse et al.). FIG. 11B shows the volume ratio between consecutive layers, where layer 1 corresponds to the outermost droplet where the bars are experimental data with the error bar representing the standard deviation and the dots are predictions calculated from the path in FIG. 11A using the lever rule. FIG. 11C shows the critical size for a droplet to harbour a higher multiplicity as function of ethanol concentration with the transition size given by the crossover between two droplet multiplicities, as shown in the inset. FIG. 11D shows the volume ratio of consecutive droplets for increasing ethanol concentration in the outer flow.

FIG. 12A is a set of stills of a movie of the spontaneous formation of a multiple emulsion through ternary phase separation, notable for the second burst of nucleation at t=7 s and how the nucleated droplets move towards the centre. FIG. 12B shows the solution at arbitrary times to the 1D diffusion equation with vanishing Dirichet boundary conditions at infinity, indicating how nucleated droplets will move towards the highest ethanol concentration in the centre of the droplet. FIG. 12C graphs surface tension between DEP and water for various ethanol volume fractions, as measured with pending drop tensiometry where the error bars indicate the standard deviation (note that the surface tension goes to zero as the ethanol concentration increases, such that at 40% the surface tension is zero and the droplet dissolves).

FIG. 13A is a set of stills of a movie in which a quintuple emulsion destabilizes in 2 stages wherein the second and fourth layer subsequently coalesce with the outside, thereby expelling layer 3 and 5 (the inset provides a side view obtained with confocal microscopy, the oil is dyed red with RITC). FIG. 13B shows the lifetime of unstable multiple emulsions as function of droplet diameter. FIG. 13C is a graph of the stability of droplets as function of surfactant concentration in the outer flow, where the pressures are measures of the flow rates for the outer flow containing the surfactant. FIG. 13D is a graph of the cumulative number of released water compartments as function of time where M=number of layers (In the inset the distribution of popping events is shown for a triple emulsion).

DETAILED DESCRIPTION OF THE PREFERRED EMBODIMENTS

Figure 2:
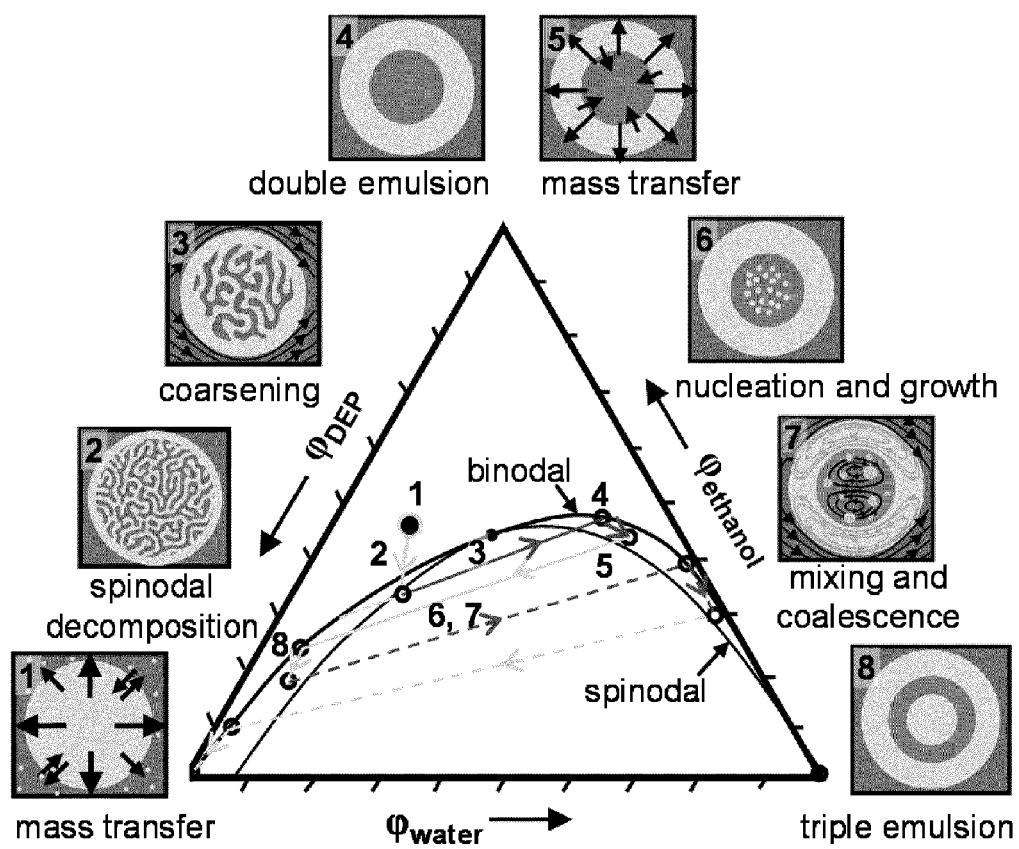
FIG. 2 illustrates the zigzag trajectory following the compositional evolution of the innermost droplet from the miscible region (1) to a triple emulsion (8), and continues until complete phase separation along the dashed line the associated schematic diagrams illustrate the stages of phase separation cycles.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

In one embodiment, spontaneous formation of multiple emulsions consists of liquid-liquid phase separation of ternary mixtures. This method allows one to stabilize submicron double emulsions, which are difficult to construct mechanically. Recent results call for an understanding of the basic principles of phase separation inside emulsion droplets. In equilibrium, ternary liquid phase separation leads to double emulsions of pure oil and water. The slow rate of mass transfer allows for local fluctuations in composition to seed multiple phase separation events within a single droplet. These kinetic pathways control the emulsion layers and open the possibility of mass production because there is no need for surface patterning, multiple channels, and complex flow fields. Multiple emulsions, or droplet within a droplet structures can be conceived of as a "onion" with each droplet forming a layer.

To this end, the quantitative dependence of the number and size of the inner droplets on the outer droplet size, initial composition of the ternary mixture, and the molecular mass of the surfactant were investigated. First the formation of emulsion layers through a single channel flow was visualized to study the mechanism of phase separation. The whole process can be mapped onto a trajectory on the phase diagram from the miscible region to complete phase separation. These emulsions serve as precursors for other particulate materials, such as polymer capsules and lipid vesicles. Additionally results show that the ternary mixture can be loaded with active ingredients for drug delivery. Finally, these high order emulsions can be coalesced into a single droplet to give lipid-stabilized droplets with ordered structures.

In one embodiment, multiple emulsions are produced by dripping a single phase ternary mixture of oil, a polar solvent, and water through a microcapillary into a water stream containing a surfactant, as depicted in FIG. 1A (see also FIGS. 5A-D). As a case study, diethylphthalate (DEP), ethanol, and water stabilized by the hydrophilic pluronic F127 surfactant (0.1 wt-%) were used, but the scope of the invention is not limited to these particular exemplary embodiments. Injecting a mixture close to the binodal line of the ternary phase diagram yields monodisperse, multiple high order emulsions. The mutual solubility of water and DEP is negligible. For purposes of allowing visualization, the process was slowed from seconds in FIG. 1B to a minute to visualize the formation of a quintuple droplet by enlarging the microfluidic device ten-fold and increase the viscosity of the continuous phase with 0.5 wt-% polyalginate. This modification does not affect the phase behaviour significantly. The initial composition of the injected ternary mixture governs droplet multiplicity, as shown in the panels in FIG. 1C. Increasing the water and ethanol content from composition (1) to (5) along the binodal line increments the number of inner droplets up to five. However, a further increase reverses the trend, as shown by the triple and double emulsions at compositions (6) and (7), respectively.

These observations can be understood in terms of the mechanism of phase separation. As the thermodynamic balance of the system changes, moving between the spinodal curve and bimodal curve, the phase separation transitions. The phase separation of composition (5) is mapped onto a zigzag trajectory on the phase diagram in FIG. 2. During droplet formation, mass transfer of ethanol and DEP occurs into the external water, whereas the exchange of water across the interface brings the surfactant in (panel 1). This mass transfer induces a compositional change in the mixture, which shifts it to a tie line in the immiscible region. Due to the proximity of the measured binodal and postulated spinodal lines near the Plait point, internal phase separation occurs via spinodal decomposition (panel 2). This process initially forms an outermost layer, which is believed to be rich in DEP. This layer slows down the mass transfer of ethanol to the continuous phase and encases the inner droplet with the pluronic surfactant (panel 3). Spinodal decomposition results in a double emulsion (panel 4) with compositions that are given by the tie line connecting the oil rich (left) and the water rich (right) side on the binodal curve. Nonequilibrium fluctuations in composition, driven by the removal of ethanol (panel 5) and the mixing induced by internal flows, seed a nucleation event inside the inner droplet (panel 6). This phase separation occurs along the next tie line via the nucleation and growth of small inner DEP droplets. The internal flow induces these droplets to mix (panel 7 and SI) and coalesce because the ethanol in the water rich phase renders the pluronic F127 surfactant inefficient.

Figure 6:
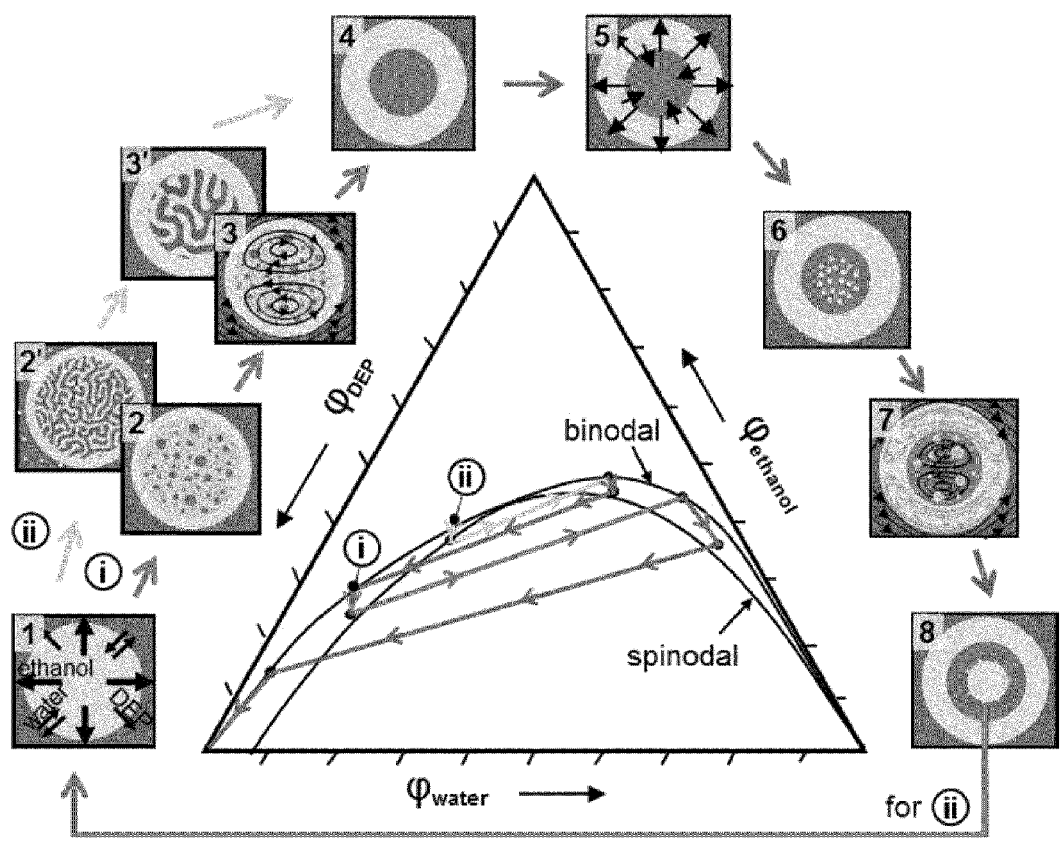
FIG. 6 depicts a schematic ternary diagram depicts alternative pathways for internal phase separation.
Figure 7:
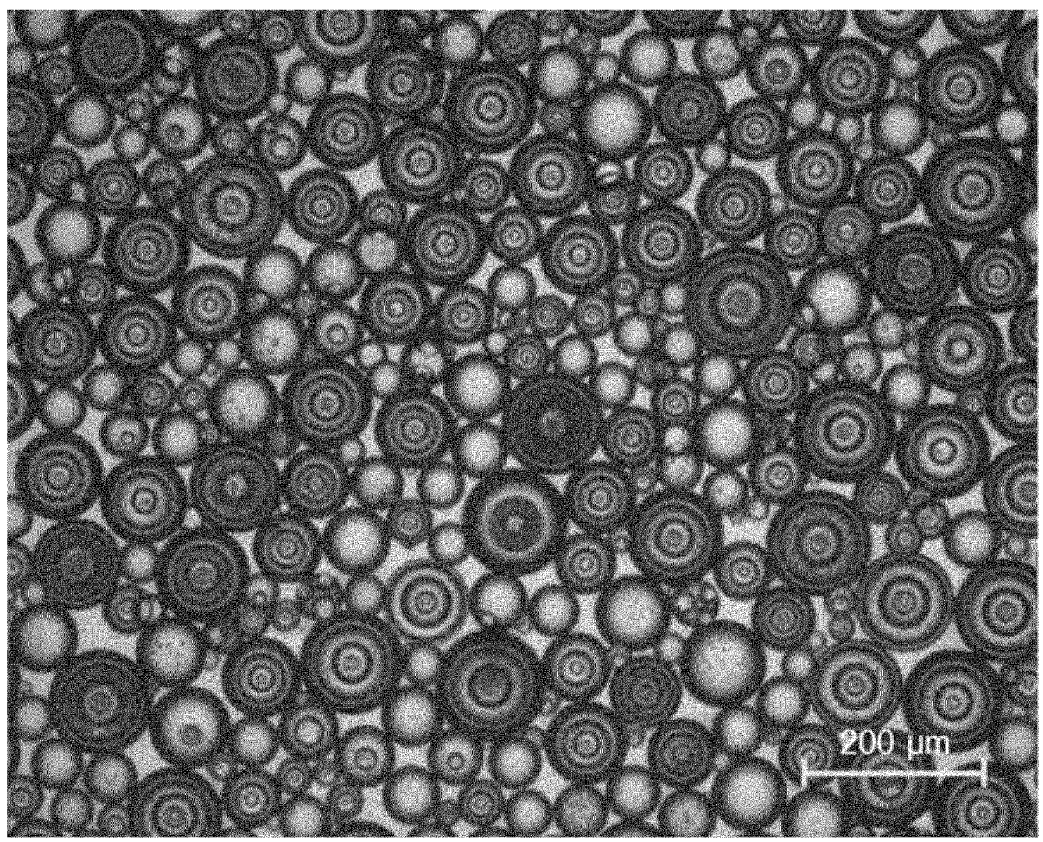
FIG. 7 shows a polydisperse multiple emulsion produced by bulk emulsification of a ternary mixture at point 5 in FIG. 1C.

Further removal of ethanol stabilizes a triple emulsion (panel 8). Subsequent cycles of phase separation that form further inner layers occur via nucleation and growth, as does starting with a composition in this region (FIG. 6). The phase separation process stops when there is no longer enough dissolved DEP and water available to form more droplets. These multiple emulsions are stable for weeks. Ternary mixtures of many other oils and polar solvents, such as acetic acid or propanol, can be used to give similar results. However, more work is needed to measure the compositions during phase separation and to obtain quantitative evidence of the observed steps. Moreover, bulk emulsification of the ternary mixture through a membrane emulsifier gives large quantities of polydisperse emulsions with variable multiplicities due to inhomogeneities in the flow (FIG. 7).

As a general rule, the highest multiplicity is achieved with the ternary composition (on the oil-rich side) whose splitting along the tie line gives rise to an inner water droplet with the highest oil content. This maximizes the number of zig-zag cycles and explains the increase in multiplicity from point (1-5) in FIG. 1C, where the tie line closest to point (5) yields droplets richest in DEP (20-30 vol %). Initial compositions at points (6) and (7) rapidly nucleate small DEP droplets that coalesce upon contact with the continuous phase, leaving less material behind for phase separation.

Figure 8:
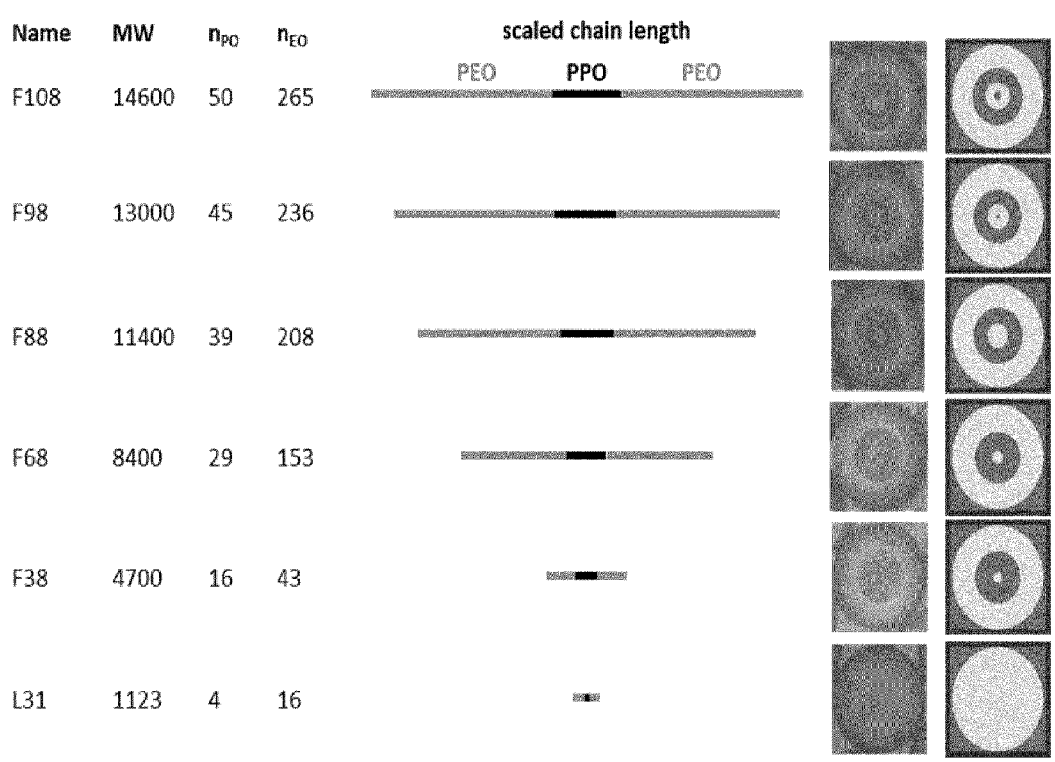
FIG. 8 illustrates an emulsion multiplicity decreases with the molecular weight (MW) in daltons of the triblock poly(ethylene oxide) (PEO) and poly(propylene oxide) (PPO), PEO-PPO-PEO, copolymer in the continuous water phase. For all micrographs the initial water content was $\varphi_0=0.12$, corresponding to point (4) in FIG. 1C in the main text.

For a given ternary liquid composition and flow rate, the multiplicity depends on the surfactant's ability to stabilize interfaces. In particular, the multiplicity in the example in FIG. 1 increases with the molecular mass of pluronic surfactants (FIG. 8). A larger surfactant, such as F127, retains more DEP through steric inhibition against coalescence of the nucleated DEP droplets with the outer layer of the same type. These droplets preferentially coalesce with each other because the rapid loss of ethanol from the outer DEP layer improves surfactant stabilization at the interface. Also, mass transfer through a layer of larger surfactant may be reduced, thus increasing multiplicity.

Figure 3A:
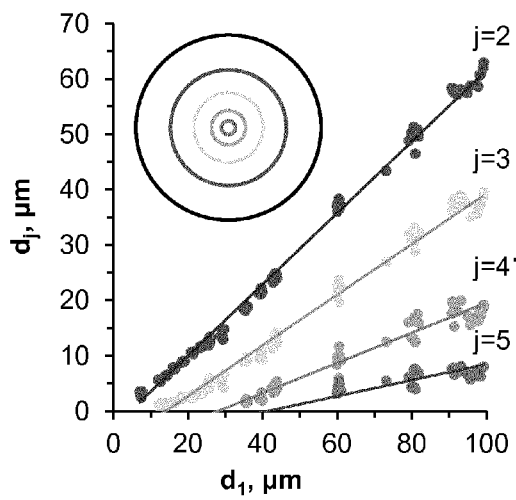
FIGS. 3A-D illustrate.
Figure 3B:
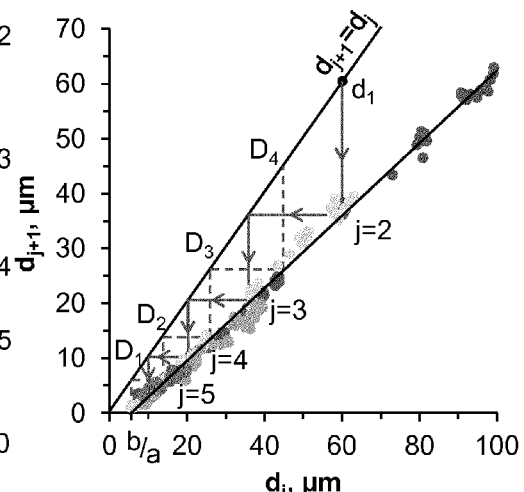
Figure 3C:
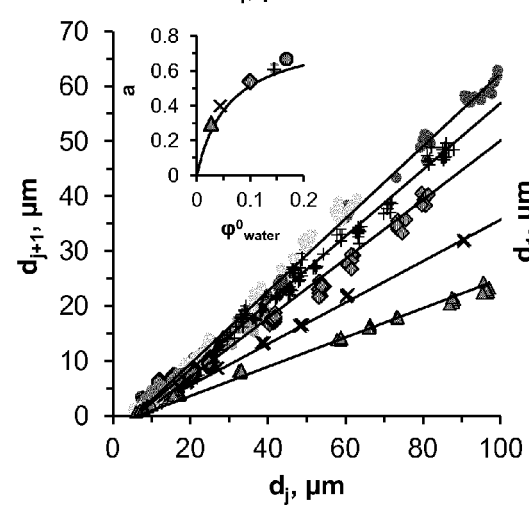
Figure 3D:
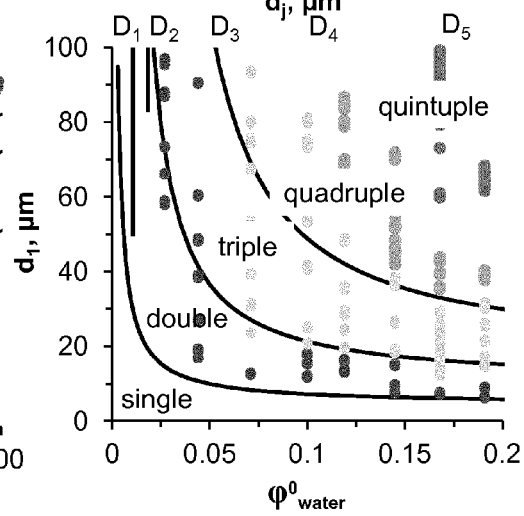

The number and diameter of the inner droplets also depend on the size of the outer droplet, $d_1$, generated by the microfluidics. For the ternary composition at point (5) in FIG. 1C the diameter $d_j$ of the $j^{th}$ inner droplet is plotted as a function of $d_1$ in FIG. 3A for j=2, 3, 4, 5, which reveals a linear relationship between $d_j$ and $d_1$. This figure also shows that the diameter $d_1$ of the outer droplet controls the multiplicity of the inner droplets. For example, $d_1$ must be larger than 5.6 µm to create a doublet (j=2) and larger than 60 µm to create a quintuplet (j=5), as shown by the intercepts in FIG. 3A. More importantly, FIG. 3B shows that all the data collapses onto a single linear mastercurve when consecutive layer diameters are plotted against each other, which implies that the process is self-similar: $d_{j+1}$ to $d_j$ like $d_j$ is to $d_{j-1}$. This line is fitted by $d_{j+1}=ad_j-b$, with a=0.66 and b=3.7 µm and it can be used to predict the multiplicity given the outer droplet diameter $d_1$. Starting from $d_1$ on the miscible line where $d_{j+1}=d_j$ the number of phase separation events down the staircase were counted between the curves $d_{j+1}=ad_j-b$ and $d_{j+1}=d_j$ before crossing the threshold value $d_j=b/a=5.6$ µm, below which no additional inner droplet can be created. This limit exists because smaller inner droplets dissolve in the oil due to their Laplace pressure. Since osmotic pressure counteracts the Laplace pressure of the inner drop, it is possible to decrease the size of the inner droplet down to micron size by applying an osmotic pressure to the droplets (FIG. 9). In order to precalculate the threshold values of $d_1$ at which the multiplicity increases, one can alternatively go up the staircase from b/a=5.6 µm. Denoting these threshold values by $D_n$ with n=1, 2 . . . this amounts to starting from $D_1=b/a$ and solving $D_1=b/a=aD_2-b$ in $D_2$ to get $D_2=b/a+b/a^2$ and so on. This gives $$D_n = \frac{b}{a} + \frac{b}{a^2} + \ldots + \frac{b}{a^n} = \frac{b}{a^n}\frac{1-a^n}{1-a}$$

$$n = 1, 2, \ldots$$

so that the final multiplicity will be j=n+1 if $D_n \leq d_1 < D_{n+1}$, as shown by the dashed line in FIG. 3B. Increasing the initial volume fraction of water $\varphi^0_{water}$ for ternary compositions along the binodal line does not alter the linear law nor the value of the intercept (b=3.5±0.5 µm), but does increase the slope a, as shown in FIG. 3C. A steeper slope implies tighter spacing between consecutive emulsion layers and therefore a higher multiplicity. In the inset in FIG. 3C once can empirically fit a = $0.84\varphi_{water}^0/ (0.065 = \varphi_{water}^0)$, which allows prediction of the multiplicity thresholds $D_n$ as a function of two experimental control parameters, the outer droplet size $d_1$ and $\varphi^0_{water}$, as shown in FIG. 3D. These 'isomultiplicity' lines capture the experimental multiplicities well, with the exception of large droplets at low $\varphi^0_{water}$, which tend to have fewer inner droplets than predicted. This overestimation is likely due to the inability of the surfactant to stabilize the innermost droplet, given that there is a decrease in the surfactant concentration towards the centre of the droplet.

Figures 4A, 4B, 4C, 4D:
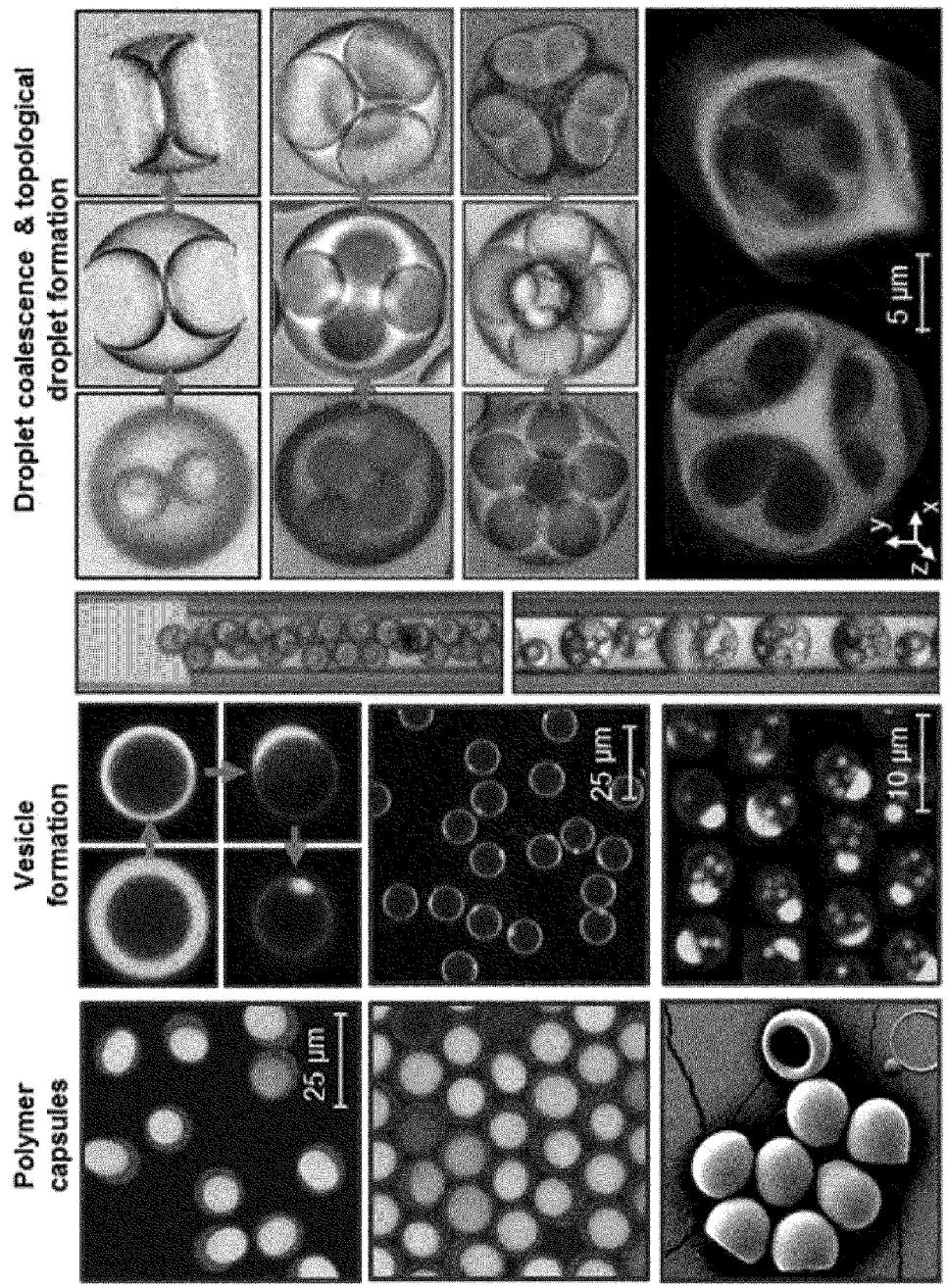
FIGS. 4A-D illustrate.
Figure 5D:
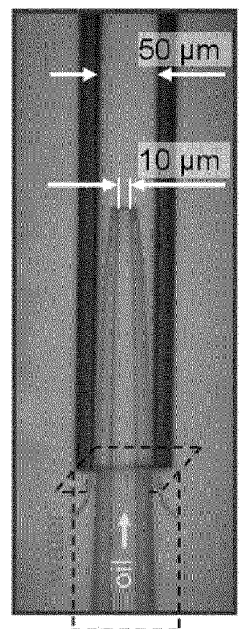
FIG. 5D shows a tapered square capillary is placed inside a round cylindrical capillary in profile.
Figure 5C:
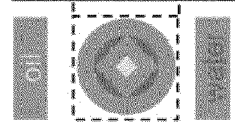
FIG. 5C shows a tapered square capillary is placed inside a round cylindrical capillary in cross section.
Figure 5B:
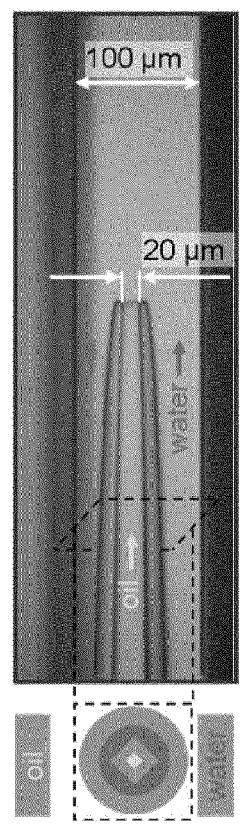
FIG. 5B shows the glass capillary microfluidic cell design in profile.
Figure 5A:
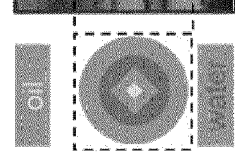
FIG. 5A shows a glass capillary microfluidic cell design in cross section.

The liquid-liquid phase separation can be applied to other surface-active materials to achieve distinct architectures. Of particular use in drug delivery is the encapsulation of molecules into water-filled biodegradable polymer shells. The ternary composition of butylacetate (BA)/ethanol/water that phase separates into a double emulsion stabilized by F127 pluronic has been empirically deduced. FIG. 4a, shows that dissolving a water insoluble polymer (e.g. polymethylmethacrylate (PMMA)) into the ternary mixture evolves into a solid PMMA capsule after the volatile BA evaporates. These capsules are deformed away from spherical by the buoyancy of the inner water and buckle on one side upon drying, as shown in the electron micrograph. Alternatively, adding phospholipids (e.g. 1,2-dioleoyl-phosphatidyl-choline (DOPC)) to the same ternary mixture and F127 pluronic yields monodisperse unilamellar vesicles in FIG. 4b. The BA begins to evaporate, dewets from the nascent lipid bilayer into a cap, which then detaches to form a separate oil droplet. This process leaves behind lipid/block-copolymer vesicles, which can be loaded with active ingredients or colloidal particles in the initial ternary mixture.

Figure 10A:
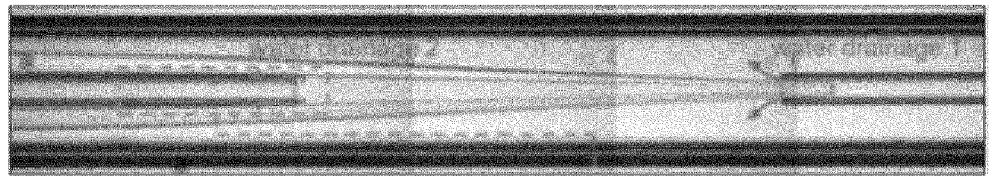
FIGS. 10A-D shows a microfluidic coalescence device.
Figure 10B:
Figures 10C, 10D:
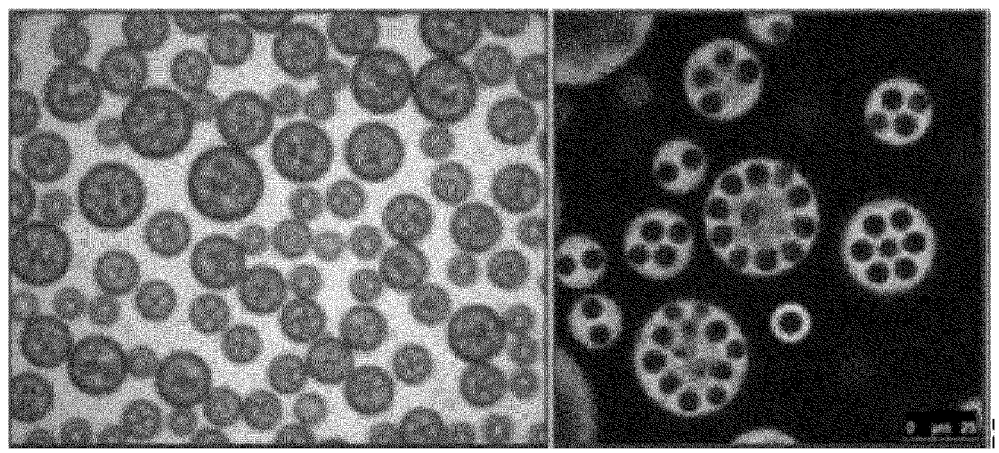

Multiple emulsions can also be used to seed droplets with complex topologies. Lipids that stabilize water-in-oil but not oil-in-water interfaces generate multiple emulsions with outermost oil layers that coalesce upon droplet contact, as shown in FIG. 4c. In particular, a ternary composition of chloroform/ethanol/water stabilized with DOPC and F127 pluronic that phase separates into triple emulsions. While the water layer is stabilized by DOPC, the inner oil droplet evaporates and the outer oil layers coalesce because the pluronic is soluble in chloroform. Concentrating these droplets in a microfluidic channel yields multiple emulsions with spatially separated droplets (FIG. 10), which have only been constructed by forced emulsification. The subsequent evaporation of 70-90% of the volume of chloroform from the outer layer changes the droplet shape into a unique geometry, which depends on the number of inner droplets, as shown in the examples in FIG. 4d. This result is analogous to the symmetry observed in colloidal clusters, except that the shape of the outer droplet is supported by bilayers, either between the inner water droplets and the continuous phase or the chloroform layer. Confocal images reveal two views of the internal structure of a chloroform droplet consisting of six water droplets. Once solidified, they can be used as compartments for biochemical reactions. These complex topologies are similar to those of microcapsules, but they are stabilized by phospholipid scaffolds.

EXAMPLES

Example Procedures

Droplets were generated in microfluidic cells consisting of a tapered square capillary. Confocal images were taken using a Leica SP5 microscope and the fluorescent dyes were excited at 464 nm and observed between 480-510 nm for FITC and 700-800 nm for nile red. The videos were taken with the Olympus CK-X-41 microscope by manually moving the stage at the flow velocity of the droplets.

Membrane Emulsification: Hydrophilic UF7R8T444 ceramic membranes (MC-Tech (Korea), 10 µm pore-width) were etched with piranha acid, coated under vacuum with tridecafluoro-1,1,2,2-Tetrahydrooctyl)trichlorosilane and subsequently washed in chloroform. The emulsification was carried out with an Internal Pressure Micro Kit IMK-20 from MC-Tech (Korea) in a stirred 1 wt-% Pluronic F127 solution.

Capsules and Liposomes: A ternary mixture of 42.5 vol-% butylacetate (BA) (10 wt-% PMMA (100 KDa, 0.02 wt-% nile red)), 42.5% EthOH and 15% H2O (0.02 wt-% FITC, 50 mM NaCl) was used to form double emulsion droplets in a continuous phase with 0.1 wt-% F127. Environmental scanning electron microscopy was performed at 2 kV with a Zeiss EV-50 microscope. A ternary mixture of 42.5 vol-% BA (0.25 g/l DOPC, 0.01 g/l 1-myristoyl-2-{12-[(7-nitro-2-1,3-benzoxadiazol-4-yl)amino]dodecanoyl}-sn-glycero-3-phophocholine (MBAD), Avanti Polar lipids, 42.5 vol-% ethanol and 15% water (200 mM Dextrose) was used to form double emulsions. The continuous aqueous phase contained 0.05 wt-% F127 and 200 mM sucrose. Carboxylate-modified microspheres (Molecular Probes, FluoSpheres) were added to the ternary mixture at 0.5 wt-%.

Complex Droplets: A ternary mixture of 43 vol-% chloroform (0.25 g/l DOPC), 43 vol-% ethanol and 14 vol-% water was injected into the continuous aqueous phase containing 0.05 wt-% F127 and 14 vol-% glycerol. Droplet coalescence occurred in a drainage device. Fluorescent lipid 1-Myristoyl-2-[12-[(7-nitro-2-1,3-benzoxadiazol-4-yl) amino]dodecanoyl]-sn-Glycero-3-Phosphocholine (MDAD) was used at a concentration of 0.01 g/l for confocal imaging in FIG. 5d.

Example 1

Formation of Droplets within Droplets

FIGS. 5A-D shows a glass capillary microfluidic cell design. A tapered square capillary is placed inside a round cylindrical capillary. The clamping of the square capillary by the inner walls of the round capillary ensures a centered alignment for the oil nozzle. The consequence of pairing square and round capillaries is that the cross-section sites are open and allow the water to enter the round outer capillary. For visualization, the layer formation process is slowed by increasing the dimensions of the microfluidic cell (channel diameter 650 µm).

FIG. 6 shows a schematic ternary diagram depicts alternative pathways for internal phase separation. The first phase separation event can occur via spinodal decomposition or nucleation and growth, depending on the position of the initial composition on the binodal line. The pathway for composition (i) undergoes nucleation and growth because the binodal and spinodal lines are sufficiently far apart, while starting from composition (ii) leads directly onto the spinodal line, as described in the main text. Further phase separation events always undergo nucleation and growth, as shown by panels 4 to 8.

FIG. 7 is a polydisperse multiple emulsion produced by bulk emulsification of a ternary mixture at point 5 in FIG. 1C. A far-reaching consequence of multiplicity control in a single step droplet extrusion process is to scale up the production of multiple emulsions from microfluidics to the bulk. As a proof of principle, controlling the pore size and flow rate of the ternary mixture through a membrane emulsifier to obtain large quantities of multilayered emulsions with a polydispersity of 65±24 µm and variability in the multiplicity.

Example 2

Multiplicity Dependence on the Surfactant

FIG. 8 shows emulsion multiplicity decreases with the molecular weight (MW) in daltons of the triblock poly (ethylene oxide) (PEO) and poly(propylene oxide) (PPO), PEO-PPO-PEO, copolymer in the continuous water phase. By varying the block composition, it can be seen that reducing the chain length of either copolymer, $n_{EO}$ or $n_{PO}$, reduces the amount of oil in the inner layers and therefore the multiplicity. As explained in the main text, this trend can be attributed to the decreasing steric stabilization capability of the surfactants. Interestingly, the F127 pluronic (MW=12500 daltons) used throughout the main paper $((EO)_{98}(PO)_{67}(EO)_{98})$ has a multiplicity of four, in agreement with the trend. For all micrographs the initial water content was $\varphi_0=0.12$, corresponding to point (4) in FIG. 1C in the main text.

Example 3

Osmotic Manipulation of Droplets within Droplets

FIGS. 9A-9C illustrates that the size of the inner water droplets can be manipulated post-emulsification. In FIG. 9A adding salt to the continuous phase (200 mM NaCl) dissolves the inner water droplet. In FIG. 9B Conversely, adding salt to the water fraction in the ternary mixture swells the inner water droplet. The graph shows the slow swelling kinetics for the 100 (bottom curve), 200 (middle curve) and 340 mM (top curve) NaCl concentration. This method can be used to form ultrathin layers of oil between the continuous phase and the encapsulated water droplet. In FIG. 9C Osmotic swelling stabilizes colloidal size double emulsion droplets (down to one micron). The inner water droplet would disappear by Ostwald ripening without salt.

Example 4

Coalescence of Multiple High-Order Emulsion Droplets

FIGS. 10A-D illustrates a microfluidic coalescence device. The continuous phase is drained away to concentrate the multilayered emulsions. A tapered square capillary is placed inside a cylindrical round capillary (ID=50 μm). The square capillary contains a second cylindrical round capillary. A stream of diluted triple emulsion droplets (o/w/o/w) first flows towards the water drainage site 1 into the square capillary, while the water drains through the four open corners, and then the droplets flow to site 2 for further water drainage. The concentrated droplets undergo several coalescence events in the cylindrical capillary, as shown by the bright field (FIG. 10C) and fluorescent confocal images (FIG. 10D) of collected droplets with multiple internal water droplets. Adding 5 mM sodium dodecyl sulphate (SDS) into the water phase stops the coalescence.

Droplet Formation-Phase Separation Bursts

The formation of an onion structure, or a droplet in droplet construct is generally described above. However, it has further been surprisingly discovered that phase separation inside the droplets occurs via multiple, consecutive events to give droplet structures that have a high interfacial energy. Moreover, the structures are concentric, which suggests an underlying organizing principle, other than gravity which usually drives spatial segregation. Multiple phase separation bursts have previously been noted in bulk experiments by Vollmer et al. in a process dubbed cascade nucleation. Their study uses a binary system, which is soluble at low temperatures, but phase separates when heated. While a sudden temperature jump leads to bulk phase separation, a slow temperature ramp gives rise to distinct bursts of nucleation. Theoretical and simulation work explain these bursts in terms of an interplay between the constant buildup of super saturation and the subsequent relaxation through either diffusive transport or a nucleation event. Even so, the final product always consists of only two continuous phases since gravity segregates and coalesces each nucleation burst.

In the case of emulsions, the miscible mixture inside the droplet undergoes a change in chemical composition, which drives the system into the immiscible region of the phase diagram. Experiments were designed to investigate whether the role of the slow temperature ramp in bulk experiments is replaced by the mass transfer rate of ethanol. Indeed, assuming ethanol leakage, the ternary phase trajectory of the phase separation events inside the droplet were quantitatively map out and find good agreement with the measured volume ratios of the inner layers. Moreover, that slowing down mass transfer increases the number of phase separation events, consistent with our hypothesis.

It is believe that order to explain the concentricity of the droplet, a surface tension gradient plays a crucial role in scooping the phase separated nuclei into the center of the droplet, independent of which phase they are in and lastly show how the same effect can be used to achieve two-step (drug) release dynamics.

The experimental setup utilized in the phase separation burst examples described herein is one deployed by Haase et al. involves a one-channel microfluidic cell, in which a ternary mixture of water, the oil Di-ethyl phthalate (DEP) and the solvent ethanol is pushed into an outer flow of water and the surfactant Pluronic F127. The composition of the ternary mixture was chosen to be in the miscible region of the ternary phase diagram (see FIG. 11A), but close to the binodal. Hence, when a ternary droplet comes in contact with the outer water flow, diffusive transport changes the droplet composition, causing it to drop below the binodal line, hence initiating phase separation. It is believed that mass transfer of ethanol from high concentration inside the droplet to low (initially zero) concentration outside the droplet is the main cause for the change in composition and hence the driving force for the thermodynamic instability that leads to phase separation. Indeed video microscopy of the droplets forming in time show that the ternary droplets shrink when they come in contact with the water reservoir, likely due to ethanol leakage. This was confirmed by measuring the droplet shrinkage as function of ethanol concentration in the water reservoir. A smaller ethanol concentration jump decreased diffusive transport and leads to slower droplet shrinkage.

So the slow diffusive transport of ethanol out of the ternary droplet has a role similar to the temperature ramp in the system of Vollmer, initiating bursts of nucleation. With video microscopy the change in droplet volume over time was measured to calculate the decrease in ethanol concentration. From the same experiment the time until completion of each phase separation is estimated so that the quench depths can be calculated. FIG. 11A shows the path through the ternary phase diagram mapped in this manner. The thickened line follows the composition of the innermost droplet, where vertical segments represent quenches due to ethanol loss and horizontal segments follow the tie lines over which the phase separation event happens. From these tie lines the relative size of the newly formed inner layer with respect to the outer droplet can be calculated using the lever rule. The results of this calculation are indicated by the red dots in FIG. 11B. Comparison with the experimental ratio between inner and outer droplet (bars in FIG. 11B) shows reasonable agreement, reinforcing our confidence in the suggested pathway.

The rate of ethanol mass transfer can hence also be used as a control parameter to vary the quench depth and through that the size and number of layers. The rate was decreased by reducing the concentration gap between the high concentration inside the droplet and the low concentration outside. As a measure for the effect of reduced quench depth on the multiplicity, the transition size is used. Evidently a larger droplet can contain more layers than a smaller droplet where the size ratio between consecutive layers is the same. The transition size describes the critical droplet size for which a higher multiplicity is achieved, given a certain ratio between consecutive layers (or a-value in terminology of Haasse et al.). FIG. 11C shows that with increased ethanol concentration and thus with decreased ethanol outflow, the transition size goes down, so the effective multiplicity increases. This can intuitively be understood in the sense that a more shallow quench allows for more bursts of nucleation and thus more layers. Accordingly FIG. 11D shows that at higher ethanol concentration the inner layers are larger with respect to the outer layers. Inversely, one would expect that a higher ethanol concentration inside the droplet would increase mass transfer and decrease the number of layers. However, this also appears to decrease the transition size (see SI). Although the phenomenon seems counterintuitive, it is logical that the ethanol concentration inside the droplet only matters as soon as the composition passes the binodal line into the meta-stable regime. Before that the mixture is stable independent of the rate of ethanol transfer. So a higher ethanol concentration inside the droplet will just artificially increase the ethanol concentration close to the droplet through mass transfer even before phase separation starts to play a role.

Interestingly, it is the same diffusive transport of ethanol that governs the concentric sphere geometry. Even without numerically solving the diffusion equation of ethanol (the 11D version of which at arbitrary times is shown in FIG. 12B as an illustration of what is going on in the 3D system), it is intuitive to see that the ethanol concentration will always decrease from a maximum in the center of the droplet to zero far away from the droplet. So during the phase separation process a spherically symmetric ethanol gradient is present throughout the droplet. FIG. 12C shows how the surface tension between DEP and water decreases as function of increasing ethanol volume fraction in the system. The result is that nuclei that form during a burst of nucleation experience a non-uniform gradient in surface tension due to the radially symmetric gradient in ethanol concentration. It can be shown that the net Marangoni force per volume element exerted on droplets in a non-uniform surface tension gradient is given by $$f(r) = \frac{2}{R} \nabla \gamma(r)$$

Here R is the radius of the nucleus and $\nabla \gamma(r)$ the position dependent surface tension gradient. The first nucleation events happen in a belt close to the border of the droplet, because the ethanol concentration will reach the critical quench depth there first. The Marangoni force will then push nucleated droplets (both oil droplets in a water phase and water droplets in an oil phase) towards the center where they will coalesce to form the next layer. The ethanol concentration will decrease in this layer as well initiating the next iteration.

This process is unique in the sense that macroscopic segregation of the two phase separated entities is not driven by gravity which is independent of the thermodynamics driving the phase separation, but by a Marangoni flow, which is inevitably coupled to thermodynamics through the ethanol concentration. Moreover, macroscopic segregation through gravity can never lead to increased complexity of the system, because the higher density phase will always go down and the lower density phase up, as is well shown by the experiments of Vollmer et al[12]. and the simulations of Cates et al[13]. Hence multiple bursts of nucleation will only create purer phases, but not change the geometry of the system. In the case of a Marangoni flow driven segregation on the other hand, the droplets are always pushed towards the center independent of their composition, so that each burst of nucleation leads to the formation of a new shell.

Droplet Destabilization

This raises the question what terminates the process of droplet formation and how the onion structure degrades or destabilizes. Harnessing and controlling destabilization of the structure will allow for controlled release of the contents of the droplets. This can be understood in terms of the Laplace pressure of multiple emulsions. The pressure of an inner droplet depends on its radius as well as on the pressure of the outer droplet as given by $P_i = P_{i-1} + 2\gamma/R_i$. Hence the pressure of the innermost droplet becomes $$P_i = P_0 + \frac{2\gamma}{R} \sum_{n=0}^{i-1} \frac{1}{a^n}$$

where i is the layer number. Result is that the pressure in the innermost droplet increases exponentially with the layer number: The third layer in a droplet with size 50 micron and a-value=0.5 has an excess inner pressure of 1.2 kPa, compared to 75 kPa for the fifth layer. Indeed, experimentally it seems that the size of the smallest inner droplet that can be stabilized inside a multiple emulsion scales with the number of layers. That is, the smallest inner droplet in a quintuple droplet will be larger than the smallest inner droplet in a triple droplet.

The resultant emulsions are stable for weeks when enough (Pluronic F127) surfactant is present to sterically protect the internal surfaces from coalescence. However when too little surfactant is available or the time it takes the surfactant to reach the surface is long, the droplets may pop, expelling the inner oil droplet and releasing the inner water volume into the outer continuous phase. Movie stills of the popping dynamics of a quintuple (n=5) droplet are in FIG. 13C. Note the long lifetime of these in principle unstable droplets. The reason for this delayed destabilization is that initially the ethanol gradient driven Marangoni effect centers the layers, thus preventing any internal coalescence. But as the ethanol gradient fades, gravity will become dominant and push the water droplet to the top of the outer oil droplet. This will bring the surfaces in close contact, allowing for coalescence.

Since the droplet lifetime is a consequence of the competition between buoyancy, which scales with droplet volume and the Marangoni force, which is a surface effect, it is believed to depend on droplet size. FIG. 12B shows that this is indeed the case. Assuming that the droplets pop when the Marangoni force equals the gravitation force one can show that—for a triangular ethanol gradient that decreases monotonically with time—the droplet lifetime scales with the radius to the power −2/3. The line (7) in FIG. 12B is a fit of this power law to the experimental data, indicating the scaling is approximately right.

So the lifetime of unstable droplets is exclusively determined by the balance between the Marangoni force and gravity, but whether or not a droplet is stable, depends on the surfactant concentration, as is shown in FIG. 13C. Clearly high surfactant concentration sterically stabilizes droplets from coalescence where a low surfactant concentration does not. However, there appears to also be an intermediate regime in which a selection of the droplets pop after a certain delay, and the rest remains stable. A possible explanation for this effect is that it takes the large polymeric surfactant time to diffuse to the surface of the droplets and organize itself there such that the droplet is sterically stabilized. This diffusion is a stochastic process so that in a narrow range of surfactant concentration the steric stabilization against coalescence is fast enough in some droplets in the sample but not in others. To gain insight in this time the surface tension of oil in water was measured over a period of ten minutes. The surface tension starts at a value close to that in absence of surfactant and reaches a plateau only after several tens of seconds depending on the concentration. This timescale indeed matches that at which destabilization typically occurs.

Thus, it should be appreciated that properties and parameters of the layered droplets and the environment it is in can alter the stability and provide for a controlled breakdown of the droplet. For example, a sextuple droplet with three inner water layers can release an active ingredient in three evenly timed doses on multiple time scales. It is possible to deliver chemicals and materials soluble in the oil of the droplet with a controlled time delay and a fixed number of release events based on the number of layers or shells.

Multiple emulsions have been regularly quoted as promising carriers for drug delivery. The delayed destabilization of these droplets could have important implications for the release process, since these structures contain confined water compartments of which the release into the continuous phase is set by the lifetime of the droplet. We show that using the size dependence of the lifetime, it is possible to obtain delayed, stepwise release of water compartments. The experimental release profiles for triple and quintuple droplets are shown in FIG. 13D.

Thus, the spontaneous formation of multilayered droplets is put forward as a unique example of ternary phase separation where the thermodynamic driving force for phase separation and the macroscopic segregation are coupled. In one embodiment, it is the slow outflow of ethanol that both continuously destabilizes the ternary mixture, initiating bursts of nucleation and causes the buildup of a spherically symmetric ethanol gradient that drives the spatial segregation into a concentric geometry. Furthermore we show how these processes enable two-step release profiles that could have applications in drug delivery.

Applications for the onion structures described herein, using the layered droplet within a droplet including various uses where a biocompatible emulsion is used as a delivery vehicle. For example, biocompatible oil droplets stabilised with lipids where nucleic acids such as DNA or a protein are grafted to the lipids. Layered droplets can be stabilized by specific surface binding molecules (outward facing) that bind to molecules at a target site, allowing the targeted binding of the droplet to a structure such as a particular cell type in a human or an inorganic compound. The compartmentalized droplet structure can contain one or more different agents to be released, such as drugs or nutrients, or chemicals. In one embodiment, the droplet has a polymer shell that dissolves in one time constant. In addition, the lipid composition on the droplet interface mimics the outer leaflet of cellular membranes, making the structure non-toxic to living tissue. Delivery of drugs, pesticides, cosmetics, or nutrients can be accomplished in a controlled manner to a target at a selected time.

In one embodiment, higher order droplets can harness the timed release to provide reactants and a "protected" reaction environment allowing chemical reactions to occur within the large droplet as internal layers (droplets) break down. This can allow for timed delivery of a resultant product that itself may be unstable and subject to decay, for example where it is desirable to provide a therapeutic drug that has an unstable form prone to reaction or breakdown.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method of creating an emulsion comprising:
passing a single phase mixture, comprising an oil, a polar solvent, and water, through a square, tapered microcapillary disposed within a round microcapillary;
passing a continuous phase stream containing water and a surfactant between the square, tapered, microcapillary and the round capillary;
dripping the single phase mixture from the square, tapered microcapillary into the continuous phase; and
phase separating the single phase mixture to form an emulsion having an order greater than 1, wherein the emulsion has at least an outermost droplet and an innermost droplet.

2. The method of claim 1 wherein the outermost droplet has a diameter of 5.6 μm and at least a doublet is formed.

3. The method of claim 1 wherein at least a triplet is formed.

4. The method of claim 1 wherein at least a quadruplet is formed.

5. The method of claim 1 wherein the outermost droplet has a diameter of 60 μm and at least a quintuplet is formed.

6. The method of claim 1 wherein phase separating includes a process selected from the group consisting of 1) spinodal decomposition and 2) nucleation and growth.

7. The method of claim 1, further comprising altering osmotic pressure.

8. The method of claim 7, wherein altering the osmotic pressure comprises adding a salt to the continuous phase.

9. The method of claim 7, wherein altering the osmotic pressure comprises adding salt to the water dripped through the microcapillary.

10. The method of claim 1 comprising draining away a portion of the continuous phase stream.

11. The method of claim 1, further comprising a second draining wherein a second round capillary is disposed within the square capillary and a second portion of continuous phase is drained between the square capillary and the second round capillary.

* * * * *